United States Patent
Lacey et al.

(10) Patent No.: US 11,027,090 B2
(45) Date of Patent: Jun. 8, 2021

(54) VAPOR COLUMN LIQUID ACCUMULATOR

(71) Applicant: GENERAL ELECTRIC COMPANY, Schenectady, NY (US)

(72) Inventors: Joseph James Lacey, Cambridge, WI (US); David Michael Wahl, Madison, WI (US)

(73) Assignee: General Electric Company, Schenectady, NY (US)

( * ) Notice: Subject to any disclaimer, the term of this patent is extended or adjusted under 35 U.S.C. 154(b) by 762 days.

(21) Appl. No.: 15/856,748

(22) Filed: Dec. 28, 2017

(65) Prior Publication Data

US 2019/0201656 A1    Jul. 4, 2019

(51) Int. Cl.
| | |
|---|---|
| *A61M 16/18* | (2006.01) |
| *F16L 55/033* | (2006.01) |
| *F16L 55/053* | (2006.01) |
| *A61M 15/00* | (2006.01) |
| *A61M 16/10* | (2006.01) |
| *A61M 11/00* | (2006.01) |

(Continued)

(52) U.S. Cl.
CPC ........ *A61M 16/183* (2013.01); *A61M 11/005* (2013.01); *A61M 15/0006* (2014.02); *A61M 16/109* (2014.02); *B67D 7/00* (2013.01); *F16L 55/0333* (2013.01); *F16L 55/052* (2013.01); *F16L 55/053* (2013.01); *A61M 16/18* (2013.01); *A61M 2205/0294* (2013.01); *A61M 2205/3331* (2013.01); *A61M 2205/3334* (2013.01); *A61M 2205/3341* (2013.01)

(58) Field of Classification Search
CPC ................ A61M 16/18; A61M 16/183; A61M 2205/3337; A61M 2205/3341; A61M 2205/3344; A61M 16/109; A61M 16/10; A61M 16/104; A61M 16/1045; A61M 5/16831; F16L 55/04–054; F16L 55/053; F04B 11/0016
See application file for complete search history.

(56) References Cited

U.S. PATENT DOCUMENTS

| | | | |
|---|---|---|---|
| 2,963,044 A | * | 12/1960 | Hellund ................ F16L 55/052 138/30 |
| 3,264,837 A | | 8/1966 | Harnish |

(Continued)

FOREIGN PATENT DOCUMENTS

CN    105351285 A  *  2/2016

OTHER PUBLICATIONS

Patent Translate: English translation of CN-105351285-A (Year: 2020).*

*Primary Examiner* — Nilay J Shah

(57) ABSTRACT

Liquid accumulators and methods for reducing pulsations of a liquid flow are disclosed. A liquid delivery system comprises a pump configured to drive liquid to a pipe. The pipe is configured to transmit a liquid flow. A liquid accumulator is fluidically connected to the pipe. The liquid accumulator comprises a chamber containing the liquid and a vapor column and a power source configured to input energy to the chamber to generate vapor from the liquid to form the vapor column. The vapor column constitutes a gas spring to reduce pulsations of the liquid flow in the pipe. The spring rate of the gas spring can be adjusted by changing the input energy level from the power source to the chamber.

18 Claims, 8 Drawing Sheets

Figure 1:
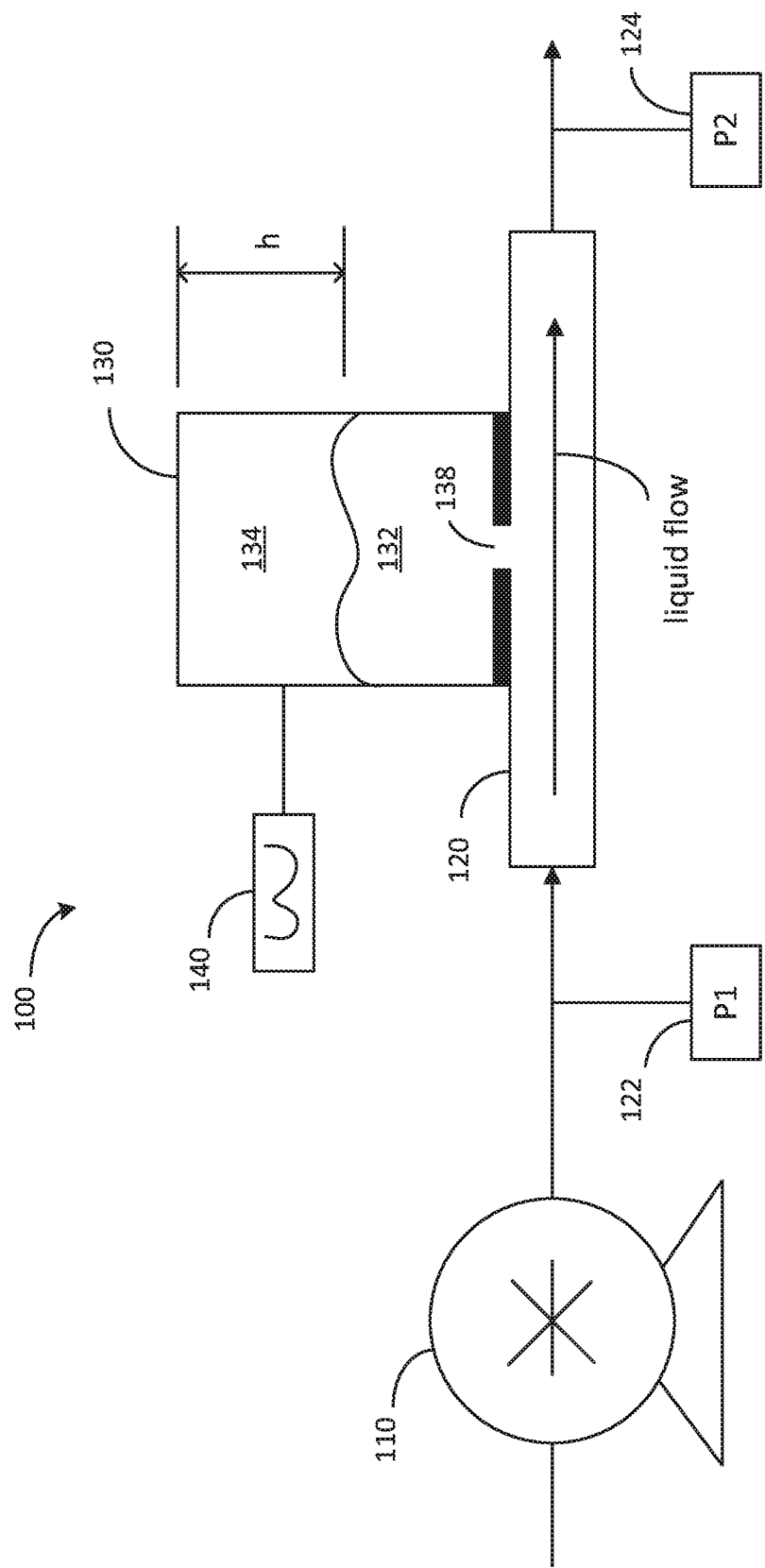

(51) Int. Cl.
*B67D 7/00* (2010.01)
*F16L 55/052* (2006.01)

(56) References Cited

U.S. PATENT DOCUMENTS

| | | | | |
|---|---|---|---|---|
| 3,532,125 | A | * | 10/1970 | Everett ................. F16L 55/054 |
| | | | | 138/30 |
| 3,636,723 | A | | 1/1972 | Kramer |
| 3,890,976 | A | * | 6/1975 | Bazell ............... A61M 25/0068 |
| | | | | 128/207.15 |
| 4,445,829 | A | * | 5/1984 | Miller ..................... F16L 55/05 |
| | | | | 137/565.34 |
| 7,121,304 | B2 | | 10/2006 | Gray, Jr. |
| 8,573,248 | B2 | | 11/2013 | Mashak |
| 2008/0275398 | A1 | * | 11/2008 | Hiebert ............... A61M 39/223 |
| | | | | 604/131 |
| 2008/0292483 | A1 | | 11/2008 | De Koning |
| 2016/0338407 | A1 | * | 11/2016 | Kerdemelidis ...... H05B 1/0244 |
| 2018/0166060 | A1 | * | 6/2018 | Grubb .................... F04C 29/06 |

* cited by examiner

VAPOR COLUMN LIQUID ACCUMULATOR

TECHNICAL FIELD

This disclosure relates to liquid accumulators and methods for reducing pulsations of the pressure of a liquid flow.

BACKGROUND

Liquid accumulators are used in various liquid delivery systems, for example, anesthesia agent delivery systems, fuel delivery systems, coolant delivery systems, etc. The liquid delivery system uses a pump (e.g., reciprocating pump) to drive the liquid into a piping to transmit the liquid flow. The pump may introduce pulsations of flow rate/pressure into the piping, which may not be desirable in many applications. For example, in an anesthesia agent delivery system, varying flow rate of the anesthesia agent in the piping can cause varying input pressure at the injector, which injects the agent into a vaporizer. Varying input pressure can lead to substantial variation of the agent vapor output rate given that the volume expansion from liquid to gas phase is huge (e.g., ~200 times expansion). Thus, a liquid accumulator is used upstream of the injector to reduce pulsations of the flow rate/pressure.

A typical accumulator includes a liquid volume and a gas volume (i.e., gas spring) separated by an object (e.g., bladder, diaphragm, or piston). The liquid volume is fluidically connected to the piping of the liquid delivery system. The gas volume is pre-charged with gas, where the amount of the charged gas dictates the spring rate of the gas volume. In operation, the gas volume is compressed during the flow output phase of the pump and expanded during pump non-delivery period. The compression or expansion of the gas volume exerts force on the liquid volume through a bladder, diaphragm, or piston that separates the gas volume from the liquid volume, and thus smoothing the pulsations of the flow rate/pressure in the piping.

Conventional liquid accumulators may have technical problems such as gas permeation, liquid leakage, seal swelling, etc. In particular, compressed gas may permeate from the gas volume through the barrier (e.g., bladder, diaphragm, piston) to the liquid volume. Liquid may leak from the liquid volume through the barrier to the gas volume. Liquid may also cause the O-ring used for sealing around the piston to swell. Solutions to these problems are generally desired.

SUMMARY

In one embodiment, the present disclosure provides a liquid delivery system. The system comprises a pipe configured to transmit a liquid flow driven by a pump. The system further comprises a liquid accumulator fluidically connected to the pipe. The liquid accumulator comprises a chamber containing the liquid and a vapor column and a power source configured to input energy to the chamber to generate vapor from the liquid to form the vapor column. The vapor column constitutes a gas spring to reduce pulsations of the liquid flow in the pipe.

In another embodiment, the present disclosure provides an anesthesia agent delivery system. The system comprises a pump configured to drive an anesthesia agent liquid from a reservoir to a pipe and the pipe configured to transmit a flow of the anesthesia agent to an injector. The system further comprises a liquid accumulator fluidically connected to the pipe. The liquid accumulator comprises a chamber containing the anesthesia liquid flow and a vapor column and a power source configured to input energy to the chamber to generate vapor from the anesthesia liquid to form the vapor column. The vapor column constitutes a gas spring to reduce pulsations of the liquid flow in the pipe.

In yet another embodiment, the present disclosure provides a method for reducing pulsations of a liquid flow. The method comprises inputting energy to a chamber of a liquid accumulator. The chamber is fluidically connected to a pipe that transmits the liquid flow. The method further comprises generating vapor from the liquid flow to form a vapor column in the chamber, and using the vapor column as a gas spring to reduce the pulsations of the liquid flow in the pipe.

BRIEF DESCRIPTION OF THE DRAWINGS

Various aspects of this disclosure may be better understood upon reading the following detailed description and upon reference to the drawings in which:

FIG. 1 is a schematic diagram of a liquid delivery system, in accordance with an exemplary embodiment;

FIG. 2 is a graph of pulsations of flow rate/pressure output from a pump, in accordance with an exemplary embodiment;

FIG. 3 is a graph of relations of nominal vapor pressure and temperature, in accordance with an exemplary embodiment;

FIG. 4A is a schematic perspective view of a liquid accumulator and a pipe which can be used in the system of FIG. 1, in accordance with an exemplary embodiment;

FIG. 4B is a cross-sectional view of the liquid accumulator and pipe of FIG. 4A along line A-A';

FIG. 5A is a schematic perspective view of a liquid accumulator which can be used in the system of FIG. 1, in accordance with another exemplary embodiment;

FIG. 5B is a cross-sectional view of the liquid accumulator of FIG. 5A along line B-B';

FIG. 6 is a schematic diagram of a liquid accumulator with a heater on the outer surface of the chamber, in accordance with an exemplary embodiment;

FIG. 7 is a schematic diagram of a liquid accumulator with a piezoelectric actuator or an ultrasound actuator, in accordance with an exemplary embodiment;

FIG. 8 is a schematic diagram of a liquid accumulator with a stirrer, in accordance with another exemplary embodiment;

FIG. 9 is a block diagram of a controller for power source, in accordance with an exemplary embodiment;

FIG. 10 is a flow chart of a method for reducing pulsations in a liquid delivery system, in accordance with an exemplary embodiment;

FIG. 11A is a graph of pulsations of flow rate/pressure of a liquid flow output from a pump, in accordance with an exemplary embodiment;

FIG. 11B is a graph of pulsations of flow rate/pressure of the liquid flow of FIG. 11A after being adjusted by the liquid accumulator, in accordance with an exemplary embodiment.

The drawings illustrate specific aspects of the described liquid accumulators and methods for reducing pulsations of a liquid flow. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of liquid accumulators and methods for reducing pulsations of a liquid flow. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide liquid accumulators and methods for reducing pulsations of a liquid flow. An exemplary liquid accumulator includes a chamber fluidically connected to a pipe that transmits the liquid flow driven by a pump. A power source (e.g., heater, stirrer, actuator, transducer, etc.) can input energy to the chamber to help vaporize the liquid in the chamber and thus create a vapor column in the chamber. The vapor column is compressed during the flow output phase of the pump and expanded during the pump non-delivery period. The compression or expansion of the vapor column can exert force on the liquid flow in the pipe, and thus smoothing the pulsations of the flow in the pipe. Additionally, by using small opening or orifice between the liquid flow and the chamber, damping action can be performed. The spring rate of the vapor column can be adjusted by changing the input energy level which varies the amount/height and the vapor pressure of the vapor column. Different spring rates may be used for different pump speeds in real time.

The liquid accumulators as disclosed herein have at least the following advantages over conventional accumulators. First, issues of gas permeation, liquid leakage, and seal swelling can be avoided because no barrier (e.g., bladder, diaphragm, piston) is used to separate the vapor from the liquid. Actually, liquid accumulators as disclosed herein require no moving part that may fatigue or wear but use a sealed container. Thus, gas sealing is simplified because the solid body of sealed container constitutes no rupture or leak points. Second, a single material can be used for the accumulator, which avoids the problem of finding combinations of liquid compatible materials. Third, conventional accumulators require pre-charged gas which puts the system under a continuous pressure. For accumulators disclosed herein, there is no need to pre-charge gas because liquid vapor functions as the gas spring. Vapor pressure can be maintained in operation and can be released when the energy input stops. Fourth, the spring rate can be adjusted by varying the energy level input to the chamber which changes the amount/height and pressure of the vapor. Thus, the spring rate can be optimized real time for different pump speeds to allow for tuned performance throughout pump operating range. Fifth, the size of the liquid accumulators as disclosed herein can be minimal and the package space can be saved. Minimal package space is desired in applications like micro fluidic designs.

Now referring to FIG. 1, a block diagram of a liquid delivery system 100 is shown, in accordance with an exemplary embodiment. In some embodiments, the system 100 is an anesthesia agent delivery system used in an anesthesia machine. In some embodiments, the system 100 is a fuel delivery system used in a vehicle. In some embodiments, the system 100 is a coolant delivery system used in a refrigerator. In some portions of the following description, examples are explained in the context of the anesthesia agent delivery system. However, it should be understood that the system 100 can be any appropriate liquid delivery system.

As illustrated in FIG. 1, in some embodiments, the liquid delivery system 100 comprises a pump 110, a pipe 120, a liquid accumulator 130, and a power source 140. The pump 110, when activated, drives the liquid from a reservoir (not shown in the present Figure) into the pipe 120. The liquid can be anesthesia agent, fuel, coolant, or any appropriate liquid. The pipe 120 transmits the liquid flow to, for example, an injector (not shown in the present Figure) for further processing. The liquid accumulator 130 is fluidically connected to the pipe 120 and can smooth pulsations of flow rate/pressure of the liquid flow in the pipe 120. The power source 140 can input energy into the accumulator 130 to create vapor column functioning as a gas spring in the accumulator 130. In some embodiments, a first flow rate (or pressure) sensor 122 is disposed upstream of the accumulator 130 for measuring the flow rate (or pressure) before being adjusted by the accumulator 130. A second flow rate (or pressure) sensor 124 is disposed downstream of the accumulator 130 for measuring the flow rate (or pressure) after being adjusted by the accumulator. It should be understood that the liquid delivery system 100 as shown in FIG. 1 is for illustration not for limitation. The liquid delivery system may include more, fewer, or different components than those shown in FIG. 1.

The pump 110 may be any suitable type of pump. In some embodiments, the pump 110 is a reciprocating pump, such as piston pump, plunger pump, diaphragm pump, and so on. The pump 110 may operate in a range of speed to draw the liquid from a reservoir into the pipe 120. Intake and exhaust strokes of the pump 110 can cause pulsations of the flow rate/pressure in the pipe 120. In some embodiments, the pump 110 is a multi-headed pump where each pump head may be out of phase thereby resulting in overlapping intake and exhaust strokes.

Figure 2:
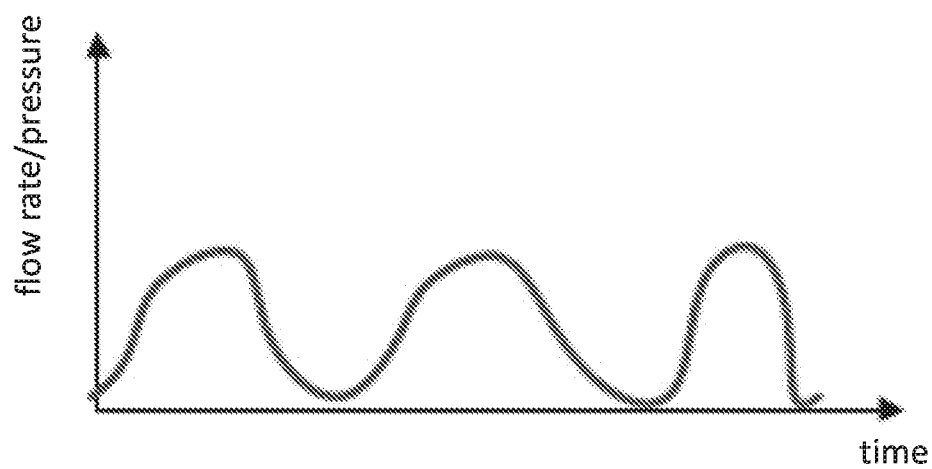

The first sensor 122 may measure the flow rate or pressure of the liquid output from the pump 110 before being adjusted by the accumulator 130. FIG. 2 shows pulsations of flow rate/pressure output from the pump 110, in accordance with an exemplary embodiment. The pulsations are undesirable in many applications. For example, in an anesthesia agent delivery system, pulsations in the pipe 120 can cause fluctuations of input pressure at the injector, which in turn can lead to substantial variation of the agent vapor output rate at the vaporizer given that the volume expansion from liquid to gas phase is huge (e.g., ~200 times expansion).

The liquid accumulator 130 is used to reduce the pulsations of flow rate/pressure upstream of, for example, the injector. As illustrated in FIG. 1, the accumulator 130 (also referred to herein as) a chamber 130 is fluidically connected to the pipe 120 through an orifice 138. Liquid occupies a portion 132 of the chamber 130. The power source 140 can input energy to the chamber 130 to vaporize the liquid in the chamber 130. The power source 140 may be for example, a heater, a mechanical stirrer, a piezoelectric actuator, an ultrasound transducer, or any appropriate power source that can add energy to the chamber 130 to help vaporize the liquid.

Vapor of the liquid occupies the rest portion 134 (with a height h) of the chamber 130—the portion 134 is also called the vapor column. The vapor column 134 functions as a gas spring to smooth the pulsations of the liquid flow in the pipe 120. In particular, during the exhaustion stroke of the pump 110, the liquid in the pipe 120 goes into the chamber 130 via the orifice 138 and the vapor column 134 is compressed (i.e., h decreases). The vapor column 134 thus exerts pressure on the liquid like a compressed spring. During the non-delivery period of the pump 100, the liquid in the chamber 130 goes into the pipe 120 via the orifice 138 and the vapor column 134 is expanded (i.e., h increases). The vapor column 134 thus exerts pressure on the liquid like an expanded spring. As such, the compression and expansion of the vapor column 134 reduce the pulsations of the flow in the pipe 120. Additionally, by using the orifice 138 between the pipe 120 and the chamber 130, damping action can be performed. Structures of the accumulator 130 and the power source 140 will be discussed in further detail with reference to FIGS. 2A through 8.

The spring rate of the of vapor column 134 may change with the energy level input by the power source 140. For example, when more energy is input to the chamber 130, more vapor is created from the liquid and the gas spring becomes "softer." In the following description, examples are explained in the context of the heat (i.e., thermal energy) input. However, it should be understood that the input energy can be any appropriate type such as mechanical energy, acoustic energy, etc.

Figure 3:
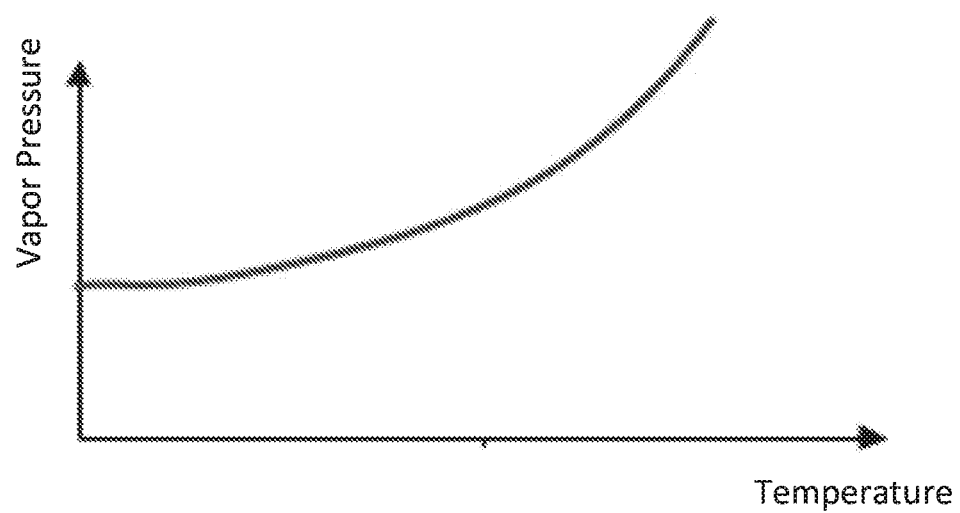

Referring to FIG. 3, the graph shows the relations of nominal vapor pressure exerted by the vapor column 134 and the temperature in the chamber 130, in accordance with an exemplary embodiment. It shows that the nominal vapor pressure increases non-linearly with temperature. The spring rate of the vapor column 134 can be expressed as:

$$k = -\frac{\Delta F}{\Delta h}, \quad (1)$$

wherein $\Delta F$ is the change of the force exerted by the vapor column 134, and $\Delta h$ is the change of the height h of the vapor column 134 due to compression or expansion. "-" indicates that the force F and the height h change in opposite directions. The force F exerted by the vapor column 134 can be expressed as:

$$F = PA \quad (2),$$

wherein P is the vapor pressure, and A is the cross-sectional area of the vapor column 134. According to the ideal gas relation, the vapor pressure P can be expressed as:

$$PV = nRT \quad (3),$$

wherein V (=Ah) is the volume of the vapor column 134, n is the amount of vapor in moles, and T is the temperature of the vapor. Based on equations (1)-(3), the spring rate of the vapor column 134 can be calculated as follows:

$$k = -\frac{\Delta F}{\Delta h} = -\frac{\Delta PA}{\Delta h} = -nRT\frac{\Delta\left(\frac{1}{h}\right)}{\Delta h} \quad (4)$$
$$= \frac{nRT}{h^2} = \frac{PV}{h^2} = \frac{PA}{h} \approx \frac{P_0 A}{h_0},$$

wherein $P_0$ is the nominal vapor pressure of the vapor column 134 under the temperature, and $h_0$ is the average height of the vapor column under the temperature. The average liquid height in the chamber 130 can be maintained at a substantially constant level in the sealed space so that the average height $h_0$ of the vapor column can be maintained at a substantially constant level for a given temperature. As equation (4) shows, the spring rate k of the vapor column 134 changes with the nominal vapor pressure $P_0$ for given A and $h_0$. The nominal pressure $P_0$ changes with the temperature as shown in FIG. 3, thus the spring rate k changes with the temperature accordingly. As discussed above, the pump 110 can operate in a range of speed. The spring rate can be optimized real time for different pump speeds to allow for tuned performance throughout pump operating range. Operation of a controller that controls the input energy level will be discussed in detail with reference to FIGS. 9 and 10.

Figure 4A:
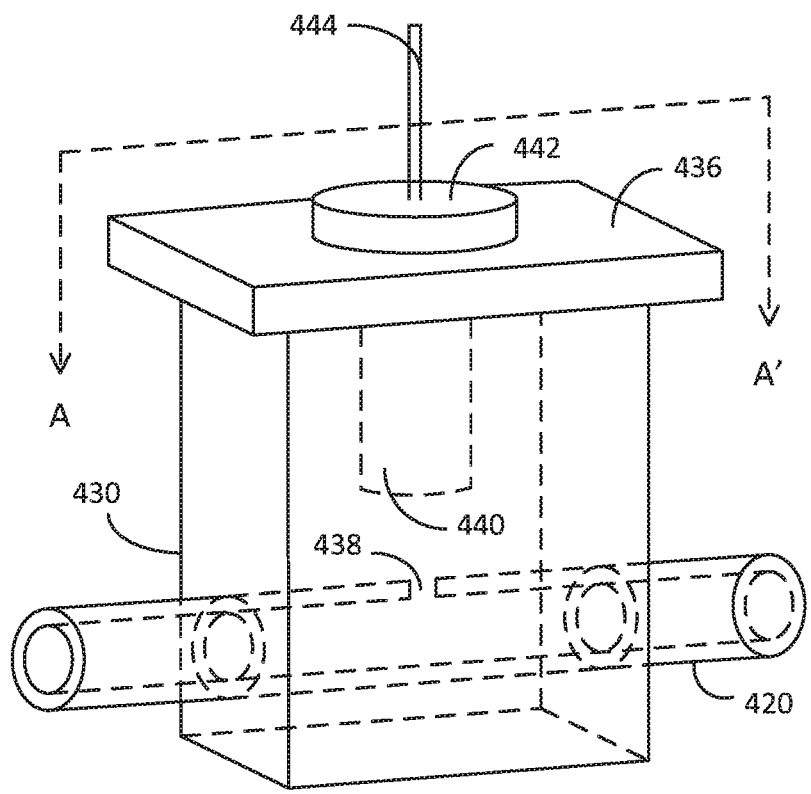
Figure 4B:
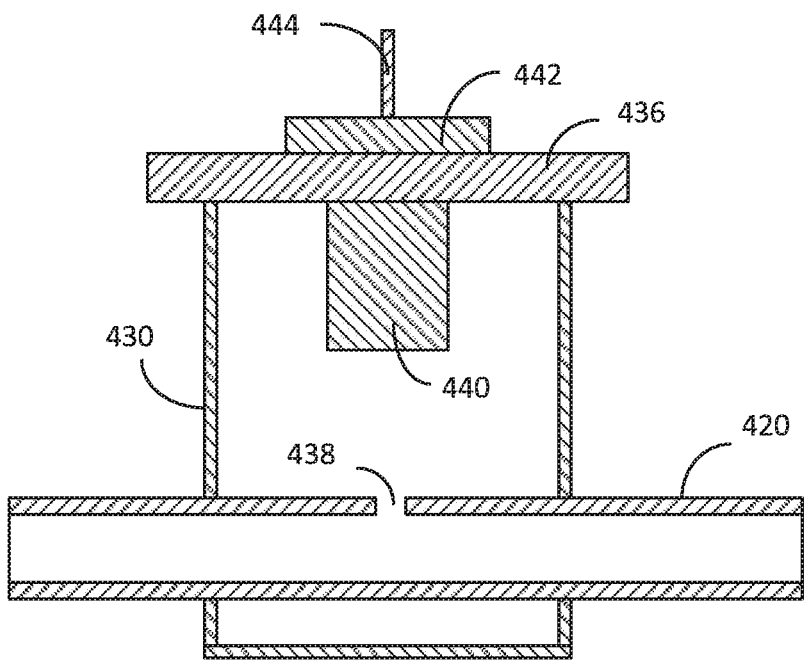

Referring to FIGS. 4A and 4B, an exemplary liquid accumulator is shown in connection with a pipe. FIG. 4A shows the perspective view of the liquid accumulator and pipe. FIG. 4B shows the cross-sectional view of the liquid accumulator and pipe along line A-A'. The liquid accumulator and pipe can be used in the liquid delivery system 100 of FIG. 1. As illustrated in FIGS. 4A and 4B, in some embodiments, the liquid accumulator comprises a chamber 430. The chamber 430 is covered by a cap 436 and hermetically sealed. The pipe 420 extends through the chamber 430 so that a portion of the pipe 420 is enclosed by the chamber 430. The chamber 430 is fluidically connected to the pipe 420 through an orifice 438 on the pipe 420. In some embodiments, the chamber 430, cap 436, and pipe 420 constitute a one-piece element constructed by, for example, casting. In some embodiments, at least one of the cap 436 and pipe 420 is a separate element and attached to the chamber 430 by, for example, glue. In some embodiments, the chamber 430, cap 436, and pipe 420 are made of the same material, for example, stainless steel, brass, PPSU plastics, or any appropriate material not to react with the liquid being delivered. In some embodiments, the chamber 430, cap 436, and pipe 420 may be made of different material.

A heater 440 is disposed inside the chamber 430 and configured to add thermal energy (i.e., heat) to the chamber 430. In some embodiments, the accumulator and pipe are constructed to ensure that the heat is not transferred to the liquid flow in the pipe 420. For example, the pipe 420 may be made of thermally insulating material to prevent the liquid flow in the pipe 420 from being heated. The heater 440 can be any appropriate type of heater made of any appropriate material, such as heating rod made of copper nickel alloy, positive temperature coefficient (PTC) thermistor made of ceramic material, etc. In some embodiments, the heater 440 is electrically to an external power supply (not shown in the present Figure) through a wire 444. The external power supply may be a direct current (DC) power supply (e.g., battery pack) or an alternating current (AC) power supply (e.g., an AC-DC adapter that can be plugged into an AC wall outlet). In some embodiments, the wire 444 is inserted into a stick 442 before entering the chamber 430 so that the chamber 430 can remain hermetically sealed.

In operation, the heater 440 heats the liquid in the chamber 430 and creates the vapor column in the chamber 430. The temperature of the chamber 430 can be controlled by controlling thermal energy level generated by the heater 440. In some embodiments, a pulse width modulation (PWM) controller may be used to control the heat generated by adjusting the duty cycle of the power (e.g., from the external power supply) provided to the heater 440. The greater the duty cycle, the more heat generated and the higher of the temperature in the chamber 430. With higher temperature, more vapor is generated which makes the vapor column "softer," as discussed above. By adjusting the heat generated, the spring rate of the accumulator can be tuned to the optimal damp pressure for different pump speed or other disturbance that causes pressure fluctuation.

Figure 5A:
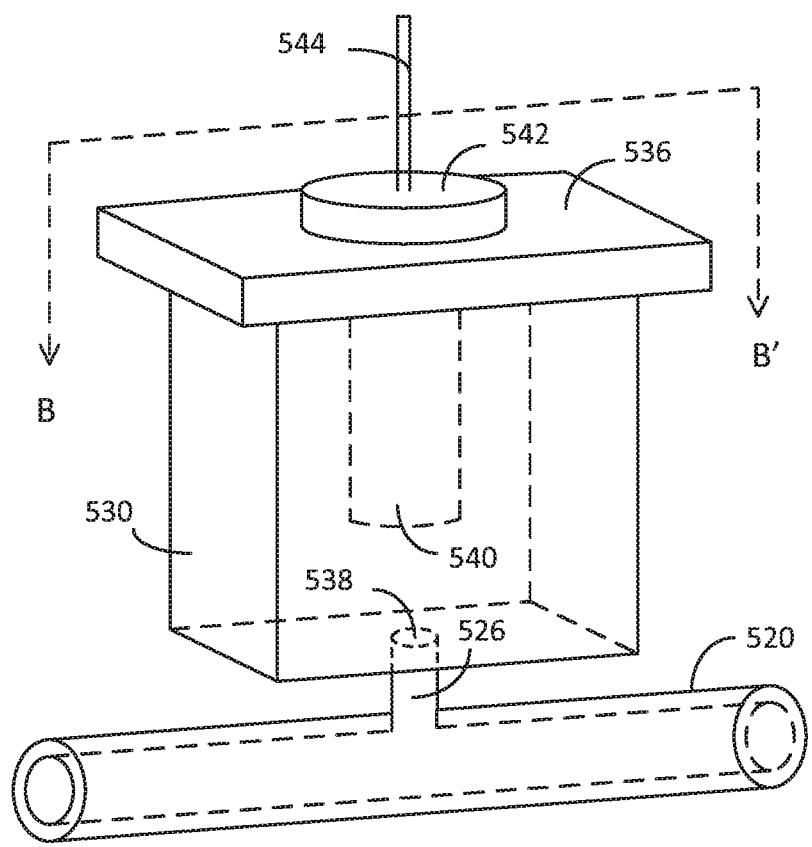
Figure 5B:
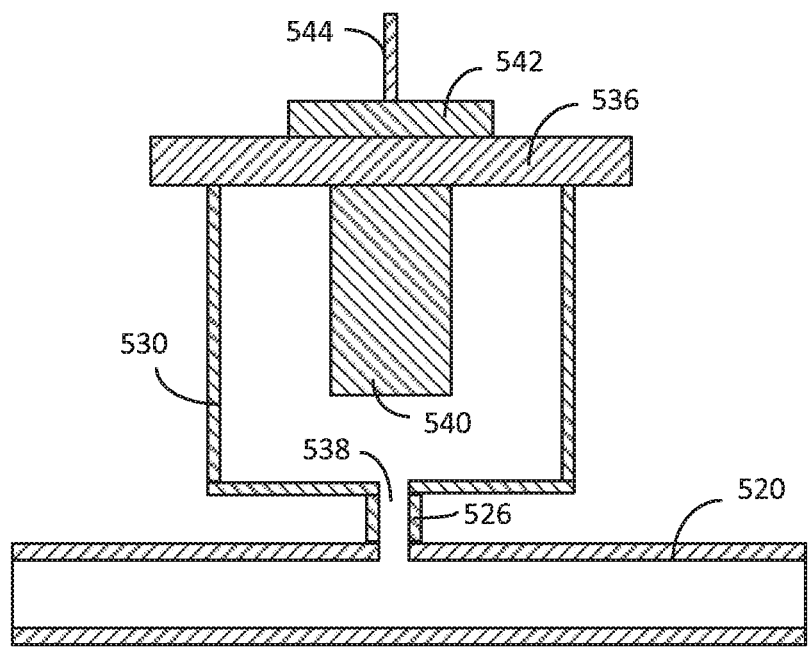

The liquid accumulator may have various structure without departing the principle and spirit of this disclosure. Referring to FIGS. 5A and 5B, another exemplary liquid accumulator in connection with a pipe is shown where the pipe is disposed outside of the liquid accumulator. FIG. 5A shows the perspective view and FIG. 5B shows the cross-sectional view along line B-B'. A chamber 530 includes an orifice 538 at the bottom. A pipe 520 that transmits liquid flow is disposed outside of the chamber 530 and fluidically connected to the chamber 530 via a flange 526. The cap 536, heater 540, stick 542, and wire 544, may have similar structure as corresponding components shown in FIGS. 4A and 4B. In some embodiments, the chamber 530, cap 536, flange 526, and pipe 520 constitute a one-piece element constructed by, for example, casting. In some embodiments, at least one of the cap 536, flange 526, and pipe 520 is a separate element and attached to the chamber 530. In some embodiments, the chamber 530, cap 536, flange 526, and pipe 520 are made of the same material, for example, stainless steel, brass, PPSU plastics, or any appropriate material not to react with the liquid being delivered. In some embodiments, the chamber 530, cap 536, flange 526, and pipe 520 may be made of different material.

Figure 6:
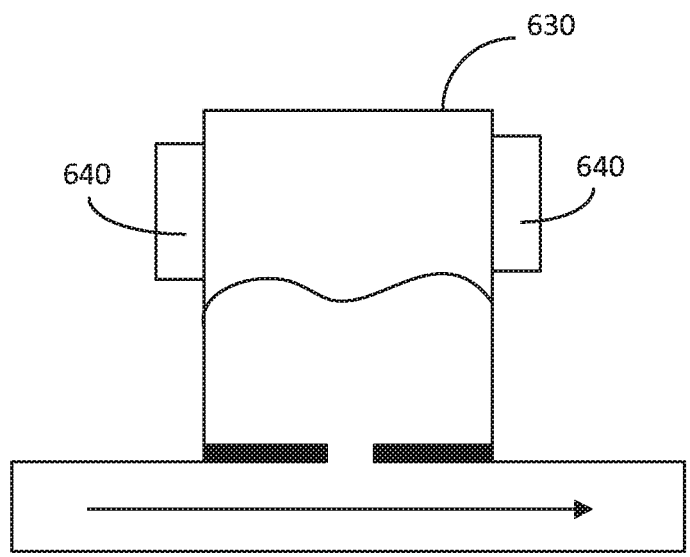
Figure 7:
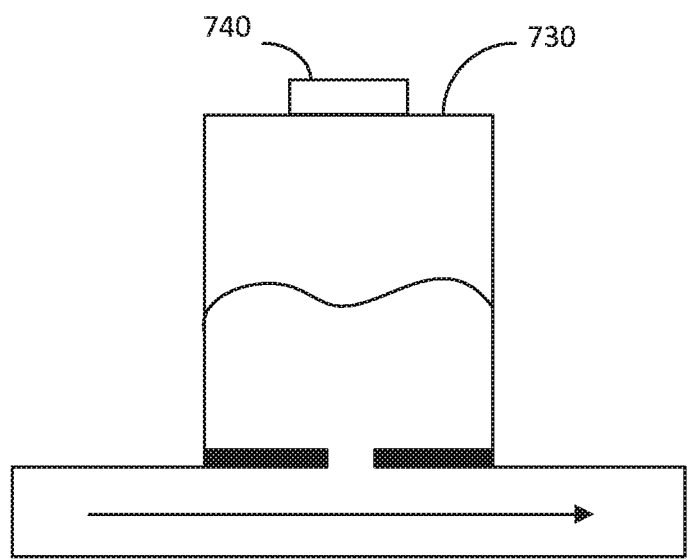
Figure 8:
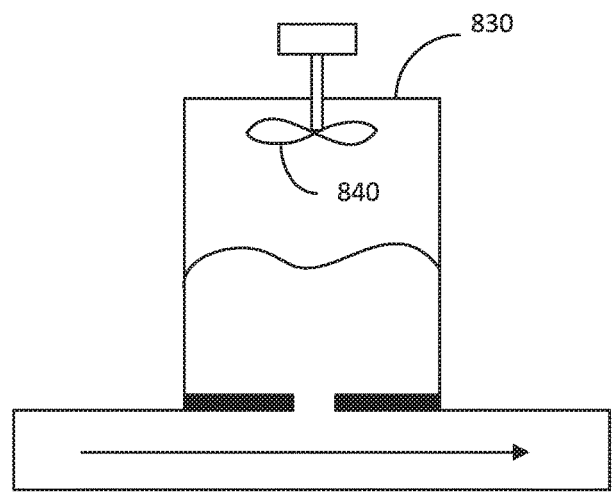

FIGS. 6-8 show more variations of the liquid accumulation. In FIG. 6, a heater 640 is disposed on the outer surface of the chamber 630. In FIG. 7, a piezoelectric actuator or ultrasonic transducer 740 is used to input energy to the chamber 730 to help generate vapor from liquid. In FIG. 8, a mechanical stirrer 840 is used to input energy to the chamber 830 to help generate vapor from liquid. In some embodiments where the liquid flow includes an anesthesia agent which may break down and release fluorine at high temperature, input energy types other than thermal energy may be desired. It should be understood that the exemplary accumulators illustrated herein are not exhaustive. A liquid accumulator can have different structure without departing the principle and spirit of this disclosure.

Figure 9:
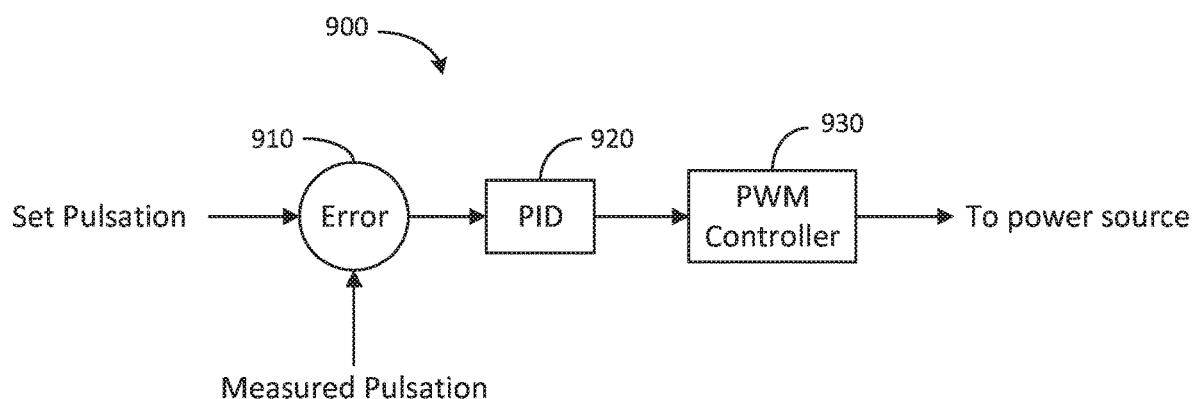

Referring to FIG. 9, a block diagram of a controller 900 for controlling a power source is shown, in accordance with an exemplary embodiment. The controller 900 is configured to control the energy input level to the chamber of the liquid accumulator. As discussed above, the spring rate and the sensitivity of the vapor column can be adjusted by changing the level of the energy input into the chamber. The higher the input energy level, the more vapor is generated and the greater the spring rate is.

As illustrated in FIG. 9, in some embodiments, the controller 900 is a feedback (e.g., closed-loop) controller which comprises a comparator 910, a proportional-integral-derivative (PID) controller 920, and a PWM controller 930. The comparator 910 compares the measured pulsation in the pipe with a pre-set pulsation. The measured pulsation can be obtained from a flow rate/pressure sensor downstream of the accumulator (e.g., the second sensor 124 in FIG. 1). The comparator 910 inputs the difference between the measured pulsation and the pre-set pulsation to the PID controller 920, which determines a duty cycle based on the difference. The PID controller 920 inputs the determined duty cycle to the PWM controller 930, which controls the energy input to the chamber based on the duty cycle. The greater the duty cycle, the higher the input energy level. And more vapor is generated which makes the vapor column "softer," as discussed above. It should be understood that the controller 900 as shown in FIG. 9 is for illustration not for limitation. An appropriate controller may include more, fewer, or different components than those shown in FIG. 9.

Figure 10:
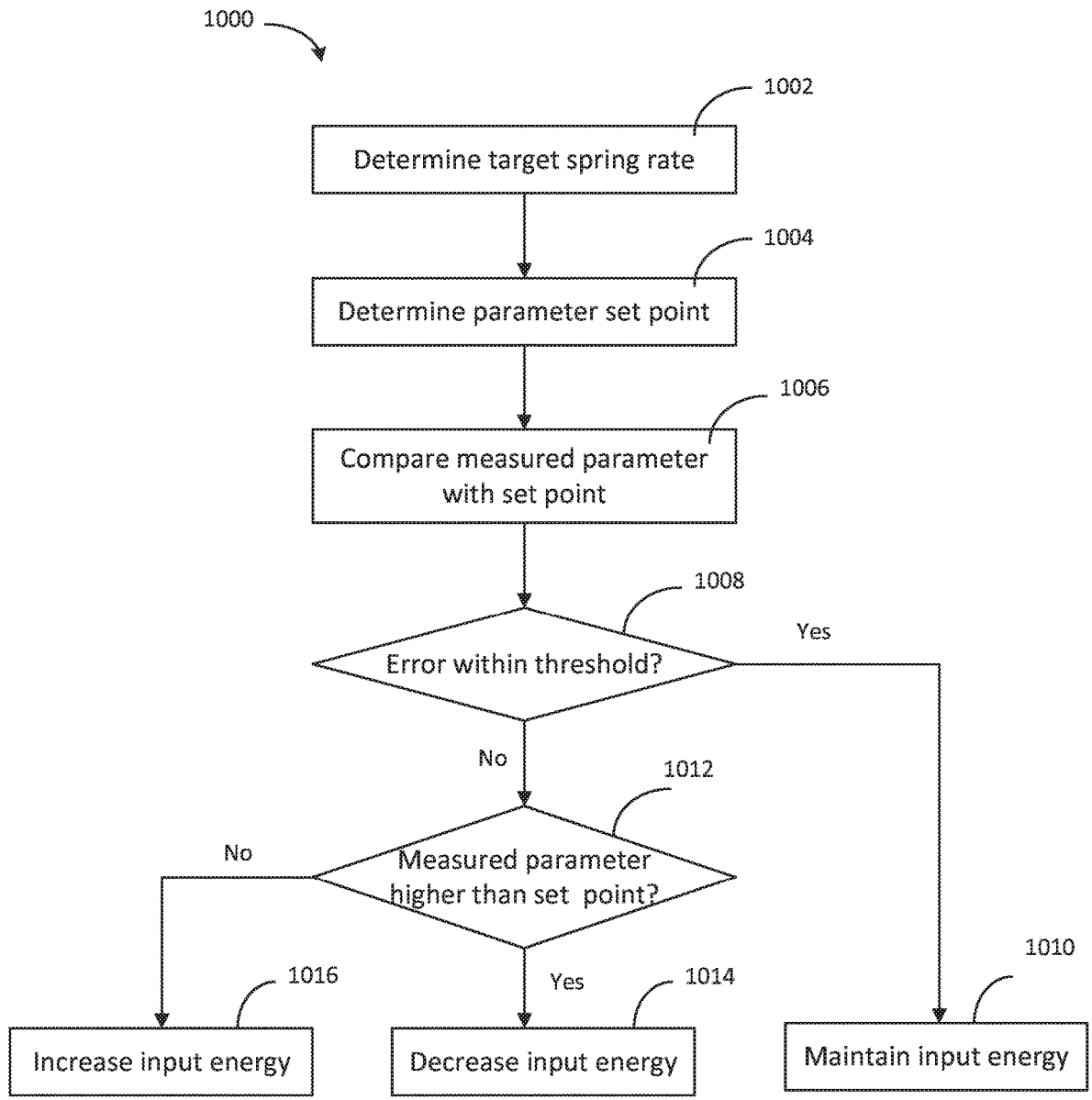

Referring to FIG. 10, a flow chart 1000 of a method for reducing pulsations in a liquid delivery system is shown, in accordance with an exemplary embodiment. The method can be executed by software, hardware, firmware, or any combination thereof to control the input energy level to the accumulator chamber. At an operation 1002, a target spring rate of the vapor column of the accumulator is determined. In some embodiments, the target spring rate is determined using a model that describes the relation between the spring rate and the pump speed. The pump speed can be measured by a speed sensor or read from a memory that stores a pre-set pump speed. In some embodiments, a look-up table stores pump speeds and corresponding spring rates. The density and viscosity of the liquid being delivered may fluctuate due to ambient temperature changes, which introduces noise into the control scheme. In some embodiments, the gas spring rate may be adjusted to compensate the fluid density and viscosity changes.

At an operation 1004, a parameter set point is determined based on the target spring rate. In some embodiments where a heater is used to add energy into the chamber, the parameter may be the temperature in the chamber. The temperature set point may be determined using the equation (4) and FIG. 3, for example. In some embodiments where a piezoelectric actuator or an ultrasound transducer is used to add energy into the chamber, the parameter may be the voltage applied on the actuator or transducer. The relation between the applied voltage and the spring rate may be obtained by using a model or through experiments. In some embodiments where a mechanical stirrer is used to add energy into the chamber, the parameter may be the stirrer speed. The relation between the stirrer speed and the spring rate may be obtained by using a model or through experiments.

In some embodiments where open-loop control is used, the input energy level is set based on the parameter (e.g., temperature, voltage, speed, etc.) set point and the process ends. In some embodiments wherein closed-loop control is used, the input energy level is further adjusted based on the feedback and operations 1006 through 1016 are performed.

At an operation 1006, the measured parameter is compared with the parameter set point. If the difference between the measured parameter and the set point is within a pre-defined threshold, at operation 1008, the energy input level (e.g., duty cycle) is maintained at the current level, at operation 1010. If the difference between the measured parameter and the set point is beyond the pre-defined threshold, at operation 1008, the process determines whether the measured parameter is higher than the set point, at operation 1012. If the measured parameter is higher than the set point, at operation 1012, the energy input level is decreased (e.g., decrease duty cycle), at operation 1014. If the measured parameter is lower than the set point, at operation 1012, the energy input level is increased (e.g., increase duty cycle) at operation 1016.

It should be understood that the process as shown in FIG. 10 is for illustration not for limitation. An appropriate process may include more, fewer, or different operations than those shown in FIG. 10.

Figure 11A:
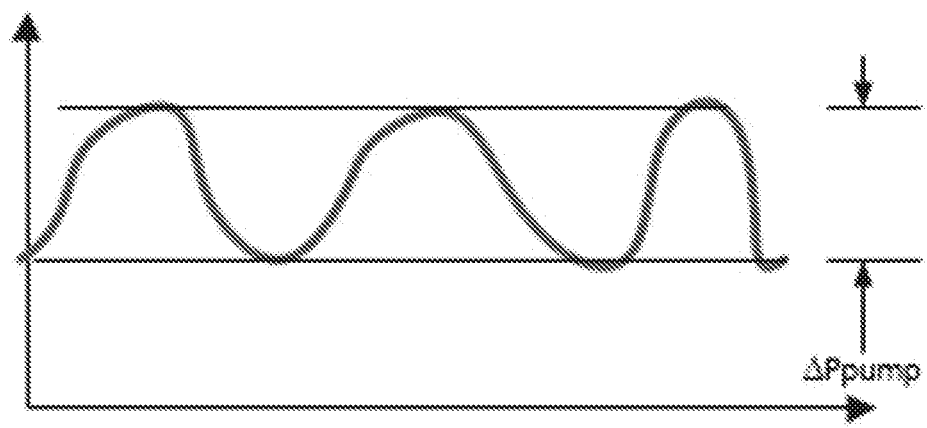
Figure 11B:
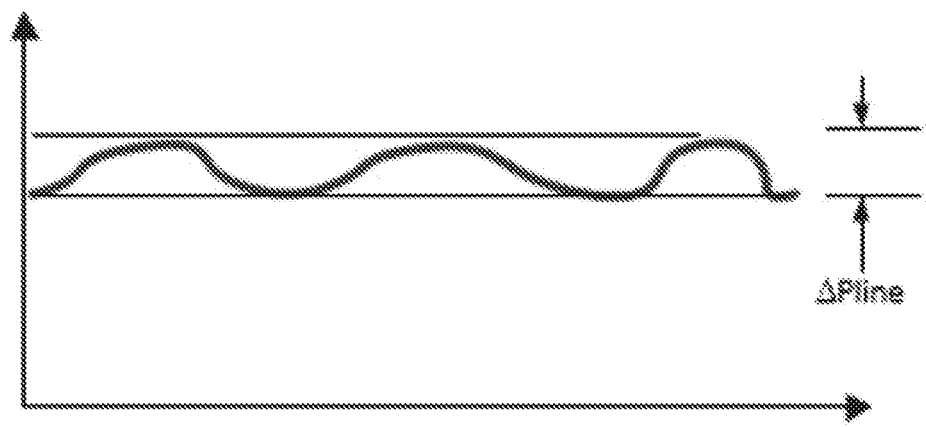

Referring to FIGS. 11A and 11B, pulsations of the flow pressure before and after being adjusted by the vapor column liquid vapor are shown, according to an exemplary embodiment. Working prototypes were built and tested, which used a PTC thermistor as a heating source for an anesthesia agent delivery system. FIG. 11 A shows a graph of pulsations of flow rate/pressure of a liquid flow output from a pump, i.e., before being adjusted by the accumulator. The pulsations were measured by a sensor upstream of the accumulator (e.g., the first sensor 122 in FIG. 1). FIG. 11B shows a graph of pulsations of flow rate/pressure of the liquid flow of FIG. 11A after being adjusted by the accumulator. The pulsations were measured by a sensor downstream of the accumulator (e.g., the second sensor 124 of FIG. 1.) The prototypes showed the reduction of pressure variation from up to ~60 psi down to ~2 psi. In the typical operating range, the prototypes showed the reduction of pressure variation from ~30 psi to ~1.5 psi.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

What is claimed is:

1. A liquid delivery system comprising:
    a pipe configured to transmit a liquid flow driven by a pump; and
    a liquid accumulator fluidically connected to the pipe, the liquid accumulator comprising:
        a chamber containing the liquid and a vapor column;
        a power source configured to input energy to the chamber to generate vapor from the liquid to form the vapor column, wherein the vapor column constitutes a gas spring to reduce pulsations of the liquid flow in the pipe; and
        a controller to supply power by the power source based on a duty cycle, wherein the duty cycle is determined based on a difference between a measured pulsation and a pre-set pulsation of the liquid flow in the pipe.

2. The liquid delivery system of claim 1, wherein the pipe extends through the chamber so that a portion of the pipe is enclosed by the chamber, and the chamber is fluidically connected to the pipe through an orifice on the pipe.

3. The liquid delivery system of claim 1, wherein the pipe is disposed outside of the chamber, the system further comprises a flange that fluidically connects the chamber and the pipe.

4. The liquid delivery system of claim 1, wherein the power source includes a heater disposed inside the chamber.

5. The liquid delivery system of claim 1, wherein the power source includes a heater disposed on an outer surface of the chamber.

6. The liquid delivery system of claim 1, wherein the power source includes at least one of a piezoelectric actuator, an ultrasound actuator, or a mechanical stirrer.

7. The liquid delivery system of claim 1, wherein the controller is to control an input energy level by the power source to the chamber, wherein the input energy level input to the chamber adjusts a spring rate of the vapor column.

8. The liquid delivery system of claim 7, wherein the controller comprises:
    a comparator configured to compare the measured pulsation of the liquid flow in the pipe downstream of the liquid accumulator with the pre-set pulsation;
    a proportional-integral-derivative controller configured to determine the duty cycle based on the difference between the measured pulsation and the pre-set pulsation; and
    a pulse width modulation controller configured to supply the power by the power source based on the duty cycle.

9. The liquid delivery system of claim 7, wherein the controller is configured to:
    determine a target spring rate based on a speed of the pump;
    determine a set point of a parameter which reflects the input energy level; and
    supply power by the power source based on the set point of the parameter.

10. The liquid delivery system of claim 9, wherein the supplying power by the power source based on the set point of the parameter further comprises:
    comparing a measured value of the parameter with the set point of the parameter;
    in response to determining that the difference between the measured value and the set point is within a pre-defined threshold, maintaining the input energy level; and
    in response to determining that the difference between the measured value and the set point is beyond the pre-defined threshold, increasing or decreasing the input energy level.

11. The liquid delivery system of claim 9, wherein the parameter is a temperature in the chamber.

12. An anesthesia agent delivery system comprising:
    a pump configured to drive an anesthesia agent liquid from a reservoir to a pipe;
    the pipe configured to transmit a flow of the anesthesia agent to an injector;
    a liquid accumulator fluidically connected to the pipe, the liquid accumulator comprising:
        a chamber containing the anesthesia agent liquid and a vapor column; and
        a power source configured to input energy to the chamber to generate vapor from the anesthesia liquid to form the vapor column, wherein the vapor column constitutes a gas spring to reduce pulsations of the flow in the pipe; and
    a controller to supply power by the power source based on a duty cycle, wherein the duty cycle is determined based on a difference between a measured pulsation and a pre-set pulsation of the flow in the pipe.

13. The anesthesia agent delivery system of claim 12, wherein the pipe extends through the chamber so that a portion of the pipe is enclosed by the chamber, the chamber is fluidically connected to the pipe through an orifice on the pipe, the chamber and the pipe are constructed as a one-piece element.

14. The anesthesia agent delivery system of claim 12, wherein the chamber is made of stainless steel, brass, or PPSU plastics.

15. The anesthesia agent delivery system of claim 12, wherein the power source is at least one of a heater, a piezoelectric actuator, an ultrasound actuator, or a mechanical stirrer.

16. The anesthesia agent delivery system of claim 12, wherein the controller is configured to control an input energy level by the power source to the chamber, wherein the input energy level input to the chamber adjusts a spring rate of the vapor column, the controller is further configured to:
   determine a target spring rate based on a speed of the pump;
   determine a set point of a parameter which reflects the input energy level;
   compare a measured value of the parameter with the set point of the parameter; and
   control the input energy level based on a difference between the measured value and the set point of the parameter.

17. A method for reducing pulsations of a liquid flow, the method comprising:
   inputting energy to a chamber of a liquid accumulator, wherein the chamber is fluidically connected to a pipe that transmits the liquid flow;
   generating vapor from the liquid flow to form a vapor column in the chamber;
   comparing a measured pulsation of the liquid flow with a pre-set pulsation;
   controlling an input energy level to the chamber based on a difference between the measured pulsation and the pre-set pulsation; and
   using the vapor column as a gas spring to reduce the pulsations of the liquid flow in the pipe.

18. The method of claim 17, further comprising:
   determining a target spring rate based on a speed of the pump;
   determine a set point of a parameter which reflects the input energy level; and
   controlling the input energy level to the chamber based on the set point of the parameter.

* * * * *